United States Patent [19]

Ragaini

[11] Patent Number: 5,108,654
[45] Date of Patent: Apr. 28, 1992

[54] METHOD FOR CONDUCTING CHEMICAL REACTIONS IN POLYPHASE SYSTEMS

[76] Inventor: Vittorio Ragaini, Via Emanuele Filiberto, 4, Milan, Italy

[21] Appl. No.: 272,442

[22] Filed: Nov. 17, 1988

[30] Foreign Application Priority Data

Nov. 20, 1987 [IT] Italy ................ 22712 A/87

[51] Int. Cl.⁵ .................. B01J 13/00; C07B 61/00
[52] U.S. Cl. .................. 252/314; 204/157.62; 204/157.85; 261/DIG. 48; 422/135; 558/369
[58] Field of Search ........ 292/314; 204/157.62, 204/157.85; 261/DIG. 48; 522/84; 210/638

[56] References Cited

U.S. PATENT DOCUMENTS

| | | | |
|---|---|---|---|
| 1,992,938 | 3/1935 | Chambers et al. | 204/157.62 X |
| 2,800,444 | 7/1957 | Hughes et al. | 204/157.62 |
| 3,245,892 | 4/1966 | Jones | 204/157.62 X |
| 3,278,165 | 10/1966 | Gaffney | 261/DIG. 48 |
| 3,346,472 | 10/1967 | Long | 204/157.62 |
| 3,755,412 | 8/1973 | Taranko et al. | 558/369 |
| 3,867,439 | 2/1975 | Hills | 562/414 X |
| 3,893,942 | 7/1975 | Yang | 585/722 X |
| 4,017,263 | 4/1977 | Holmes et al. | 585/731 X |
| 4,132,666 | 1/1979 | Chikatsu et al. | 252/314 X |

*Primary Examiner*—Richard D. Lovering
*Attorney, Agent, or Firm*—Parkhurst, Wendel & Rossi

[57] ABSTRACT

A method and apparatus for conducting chemical reactions in polyphase systems by using emulsifying means for the liquid components consisting of ultrasound emitters or turbines, in the absence or presence of a solid catalyst in fixed bed form with which the emulsified liquid components are brought into immediate contact by continuous circulation.

5 Claims, 7 Drawing Sheets

METHOD FOR CONDUCTING CHEMICAL REACTIONS IN POLYPHASE SYSTEMS

FIELD OF THE INVENTION

This invention relates to a method and the relative apparatus for conducting chemical reactions between two or more partially or totally immiscible liquids or between liquids and gases by the use of emulsifying means consisting of ultrasound or turbines, in the presence or absence of a solid catalyst.

PRIOR ART

Reactions in liquid-liquid, gas-liquid, gas-liquid-solid and liquid-liquid-solid polyphase systems are currently conducted in apparatuses of various kinds such as:
 tubular reactors, with or without packing, with cocurrent or countercurrent flow;
 tubular reactors with atomization;
 batch reactors with blade or turbine stirring: these reactors are used not only for liquid-liquid reactions (especially in the production of fine chemicals) but also for liquid-solid and liquid-liquid-solid reactions with the solid, often a catalyst, dispersed in the liquid. These latter reactors are then known as slurry reactors.

Descriptions of reactors of the prior art can be found for example in:
H. F. Rase: Chemical Reactor Design for Process Plants - Vol. 1, pp 640-659, J. Wiley (1977);
O. Levenspiel: Chemical Reaction Engineering. Second Ed., p. 421, J. Wiley (1972);
Y. T. Shau: Gas-Liquid-Solid Reactor Design, McGraw-Hill (1979);
P. A. Ramachandran and R. V. Chandhary: Three-Phase Catalytic Reactors, Gordon and Breach Science Pub. (1983);
R. S. Davidson, A. M. Patel, Ali Safdar and D. Thornthwaite, Tetrahedron Letters, 24 (52), 5907 (1983);
T. D. Lash, D. Berry, J. Chem. Eng., 62 (1), 85 (1985);
K. S. Suslick: Ultrasound in Synthesis, Modern Synthetic Methods 1986, Vol. 4, Ed. R. Scheffold, Springer-Verlag;
Sung Moon, Chem. Tech., July 1987 p. 434.

SUMMARY OF THE INVENTION

The present invention relates to a method and relative apparatus for conducting chemical reactions between two or more partially or totally immiscible liquids or between liquids and gases.

The method is characterised by being conducted using emulsifying means for the liquids consisting of ultrasound or turbines, in the absence or presence of a solid catalyst in the form of a fixed bed with which the emulsified liquids are brought into immediate contact by continuous circulation.

The apparatus comprises a liquid container provided with heat transfer means and with a system for continuously circulating liquids in the container, and is characterised by comprising one or more ultrasound emitters or a turbine able to emulsify the liquids and, if present, a tubular device containing a solid catalyst in fixed bed form situated in immediate contact with the liquid which is emulsified and continuously circulated.

Liquid-liquid-solid reactors with the catalyst arranged in a fixed bed, as in the present invention, have considerable advantages over slurry reactors. Firstly, they enable continuous or semicontinuous processes to be conducted without having to remove the catalyst, so that filtration is not required to remove the catalyst at the end of every cycle. Again, they prevent catalyst loss deriving from mutual abrasion of the suspended solid particles, as happens in the case of slurry reactors.

In addition the method of the present invention results in surprisingly high reaction rates and conversion yields compared with methods of the known art.

Preferred embodiments of the invention are described in detail by way of illustration.

One embodiment of the invention relates to reactions between two or more partially or totally immiscible liquids conducted by treating the liquid system with ultrasound in the absence of a catalyst.

A further embodiment of the invention relates to reactions between two or more partially or totally immiscible liquids conducted by treating the liquid system with ultrasound or with turbines to obtain emulsification and then bringing the emulsified liquid into immediate contact with a solid catalyst in fixed bed form.

Using the method and apparatus of the invention other polyphase reactions such as gas-liquid-solid and liquid-solid reactions can be conducted.

BRIEF DESCRIPTION OF THE DRAWINGS

Embodiments of apparatuses for implementing the method of the invention are shown in FIGS. 1 to 5.

DETAILED DESCRIPTION OF THE PREFERRED EMBODIMENTS

Figure 1:
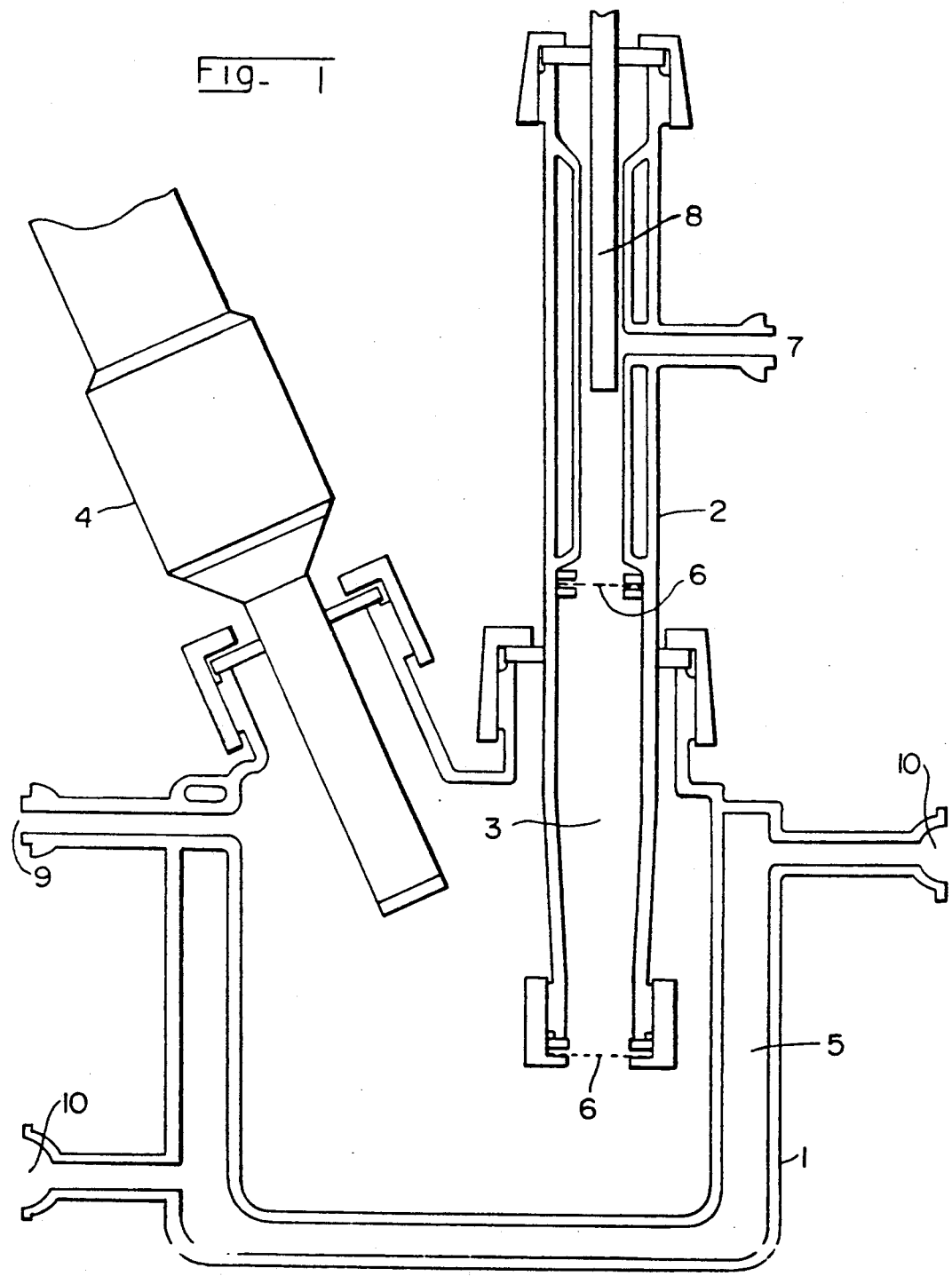
FIG. 1 shows a two-liquid emulsification and reaction apparatus which can be used with or without catalyst 3.
Figure 2:
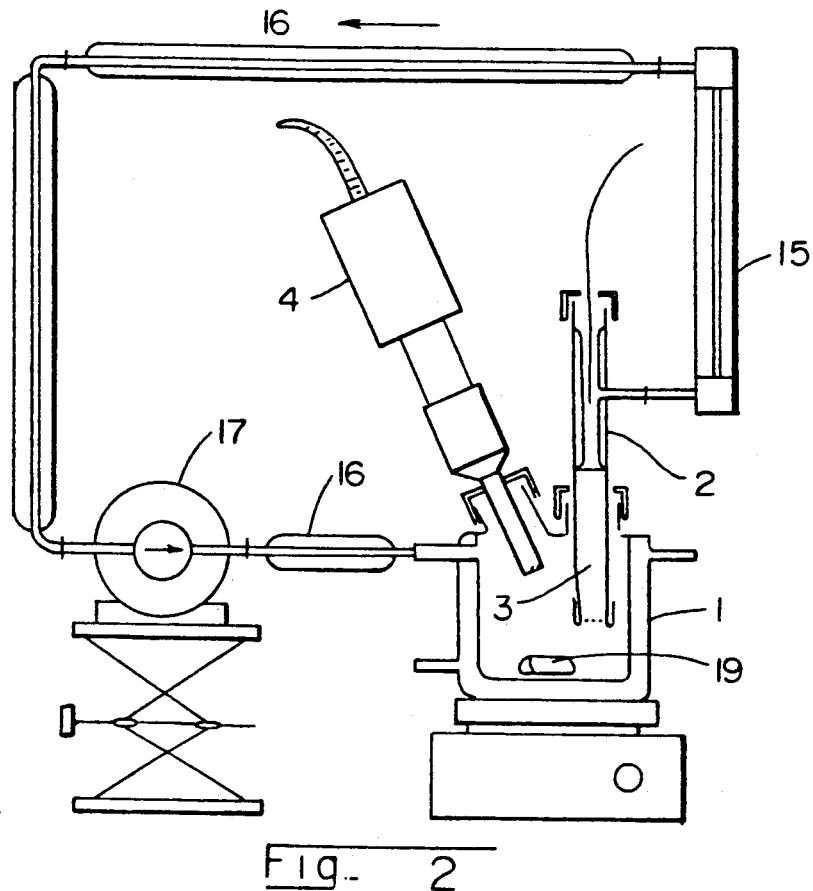
FIG. 2 shows a complete plant comprising the apparatus of FIG. 1, with liquid recirculation.
Figure 3:
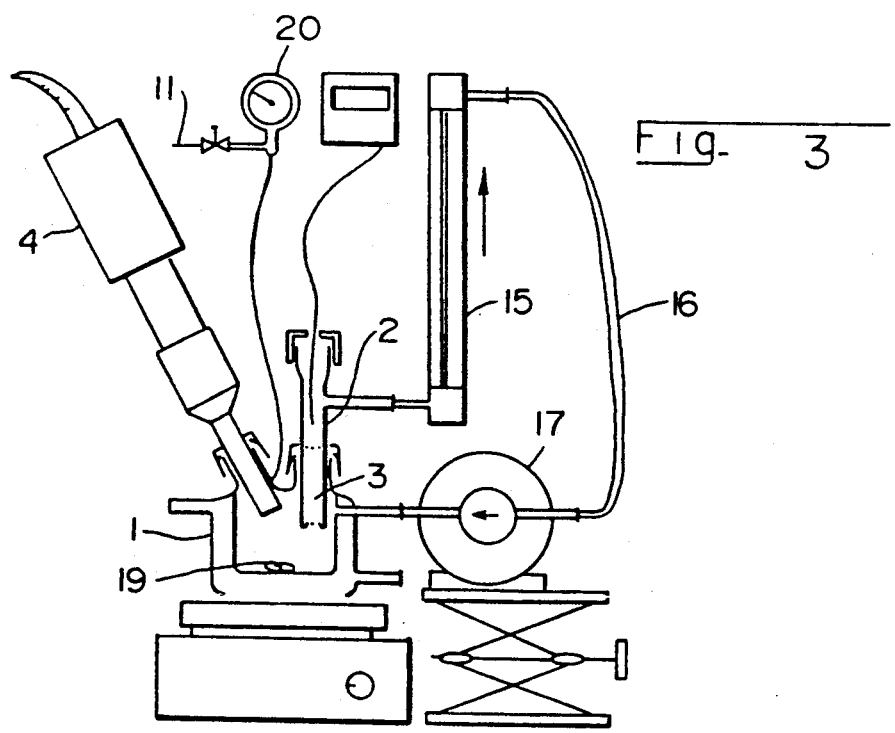
FIG. 3 is analogous to FIG. 2 and is provided for reactions in which the reaction mixture has high vapour pressure, therefore requiring pressurization which is done through the line 11 and is monitored by the pressure gauge 20.

With reference to the figures, in which identical reference numerals have the same significance, in FIGS. 1, 2 and 3 the reference numeral 1 indicates a container for treating the system with an ultrasound emitter or a turbine, both being indicated by 4, and which act directly on the liquid. The container comprises a jacket 5 with an inlet and outlet 10 for heat transfer liquid.

If present, the tubular device 2 containing the catalyst 3 arranged in a fixed bed in the space defined by the grids 6 is applied to the container 1. The device 2 is immersed in the liquid in the container 1.

In this embodiment, the ultrasound emitter 4 or turbine 4 therefore acts directly within the actual liquid container 1 housing the tubular device 2 containing the catalyst.

The liquids concerned in the reaction both enter through 9 and leave through 7. The reference numeral 8 represents a temperature indicator.

The liquid is recirculated by the pump 17 through a flow meter 15 and a recirculation line 16.

A magnetic stirrer 19 can be inserted into the container 1.

If a gaseous substance is involved in the reaction the line 11 and pressure gauge 20 are used. The apparatus of FIG. 4 consists of two coaxial tubes 22 and 23. A solid catalyst 27 arranged in a fixed bed can, if required, be disposed in the interspace between the tubes. Ultrasound emitters 26 are positioned in the sector 21 and act through the wall in contact with the liquid. The emitters can also transmit ultrasound directly into the compartment 22, not through the outer wall bounding the compartment 22. The liquids concerned in the reaction enter through the inlets 24 and leave through the outlets 28, a heat transfer liquid flowing through 25 and 29.

Figure 5:
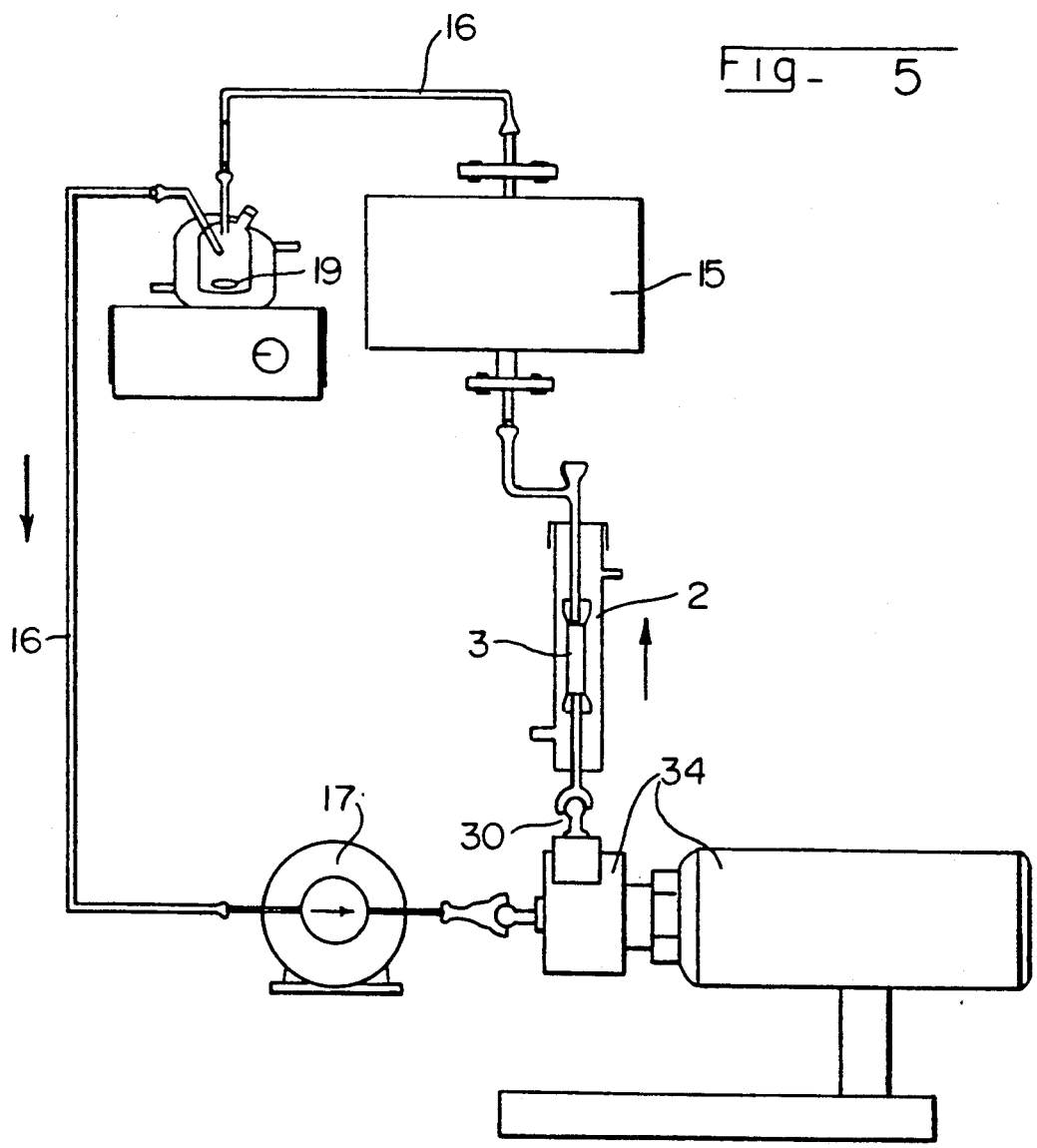
FIG. 5 shows a plant in which the liquid is emulsified by a turbine 34, and using catalyst 3.

The apparatus of FIG. 5 is a modification of the apparatus shown in FIGS. 1 and 2. In the apparatus of FIG. 5, the tubular device 2 with the fixed bed catalyst 3 does not dip into the liquid container but instead is positioned immediately on the delivery side 30 of the turbine emulsifier 34. The liquids are premixed by a magnetic stirrer 19 and circulated by a pump 17, the circulating flow rate being measured by the flow meter 15.

The present invention has been verified for the monoalkylation of phenylacetonitrile (PAN) in a reaction system consisting of an organic phase and an aqueous phase, with or without a fixed bed catalyst, in accordance with the equation:

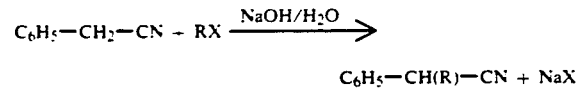

$$C_6H_5-CH_2-CN + RX \xrightarrow{NaOH/H_2O} C_6H_5-CH(R)-CN + NaX$$

in which R is a $C_1-C_{10}$ alkyl radical and X is a halogen.

The reactants are dissolved in an organic solvent chosen from the group consisting of non-halogenated or halogenated aromatic, aliphatic, alicyclic or heterocyclic solvents; ketones, ethers, amines and amides. The solvent preferably used is toluene.

An aqueous NaOH solution of between 5 and 60% concentration by weight is added.

The molar ratio of phenylacetonitrile to alkylating agent is between 0.1 and 1 and the molar ratio of phenylacetonitrile to NaOH is between 0.01 and 0.1.

The molar ratio of PAN to insoluble catalyst is between 10 and 200. With certain soluble catalysts this ratio can have a maximum value of 10,000.

The mixture is heated to a temperature of between 30° C. and 90° C. and is treated with ultrasound at a frequency of between 5 and 500 KHz or with a turbine rotating at a speed of between 2000 and 25,000 r.p.m.

The mixture is brought into immediate contact with a catalyst consisting of a quaternary ammonium salt chemically bonded to crosslinked polystyrene and arranged as a fixed bed.

If gaseous phases are not involved, the described method is conducted in the apparatuses shown in FIGS. 1, 2, 4 and 5 with liquid recirculation at a specific throughput of between 0.1 and 100 l/h per g of catalyst for a time of between 10 and 300 minutes.

If gaseous phases are involved, the apparatus shown in FIGS. 1 and 3 is used.

Figure 4:
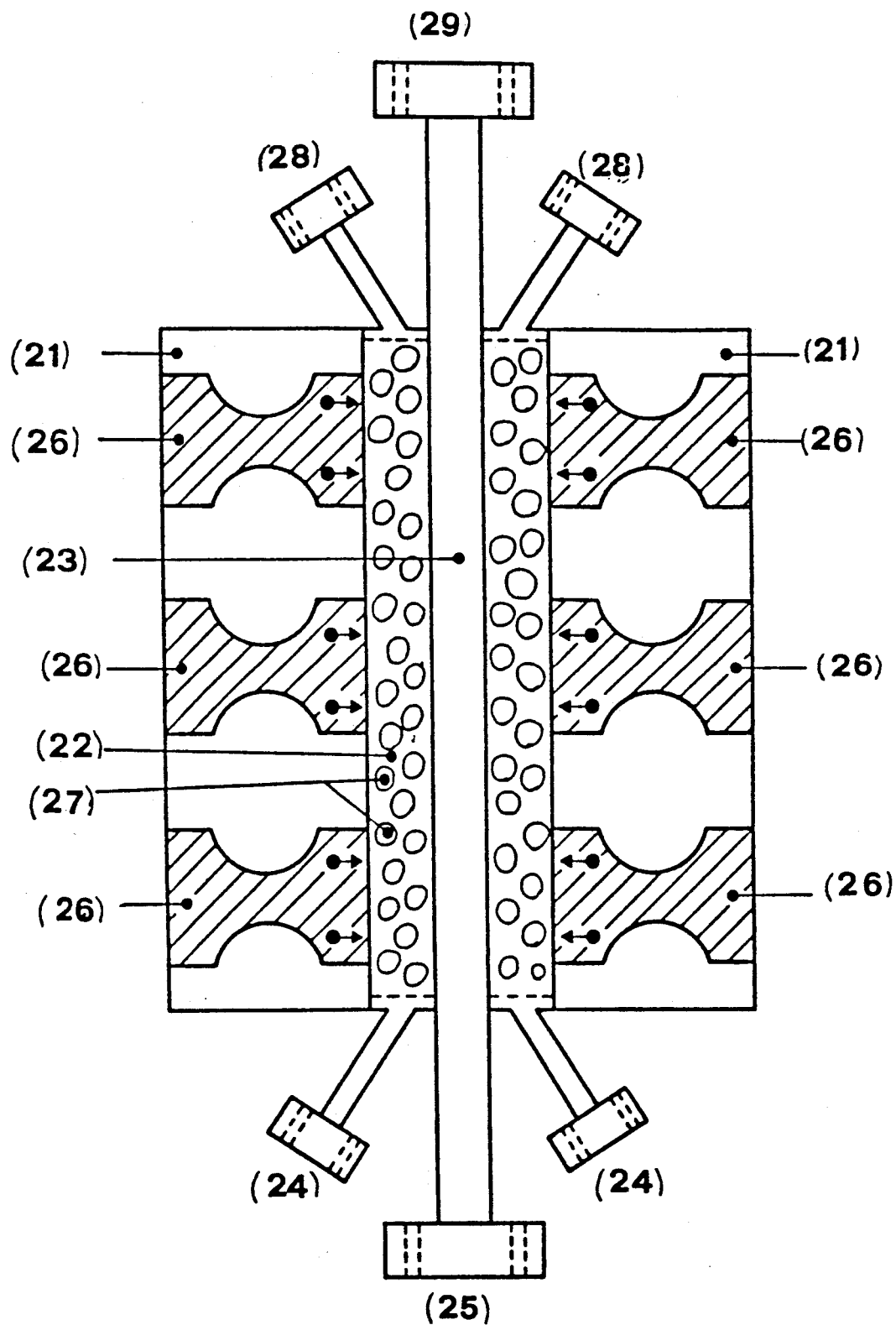
FIG. 4 is a further embodiment of a two-liquid emulsification and reaction apparatus which can be used with or without solid catalyst 27.

The method can also be conducted without catalyst, using the apparatuses of FIGS. 1, 2 and 4 at a temperature of between 30° C. and 90° C., with ultrasound treatment at a frequency of between 5 and 500 KHz for a time of between 10 and 300 minutes.

The following examples are given by way of non-limiting illustration of the invention.

EXAMPLE 1

33.7 g of phenylacetonitrile (indicated hereinafter as PAN), 197.2 g of butyl bromide and 92 g of toluene were fed into the container 1 of the apparatus of FIGS. 1 and 2, and 273 g of a 50% w/w NaOH solution were added to this mixture.

The fixed bed catalyst 3 consisted of 4.2 g of triethylbenzyl-ammonium chloride (indicated hereinafter as TEBA) chemically bonded to crosslinked polystyrene.

The liquid mixture was heated to 70° C., treated with ultrasound at a frequency of 20 KHz and circulated through the catalyst 3 at a flow rate of 20 liters/hour.

The progress of the reaction in this example and in the subsequent examples up to Example 7 was measured by determining the kinetic constant K expressed in $\min^{-1} \text{mol}^{-2} \text{l}^2$. In this example K was found to be $4.21 \times 10^{-2}$.

EXAMPLE 2

Example 1 was repeated using the following quantities: PAN 31.9 g; $C_4H_9Br$ 197.3 g; toluene 38.8 g; 50% NaOH solution 244.8 g; TEBA 4.2 g. The ultrasound treatment was replaced by treatment with a turbine rotating at a speed of 16,000 r.p.m. K was found to be $1.59 \times 10^{-2}$.

EXAMPLE 3 (COMPARISON)

Example 1 was repeated using the following quantities: PAN 9.56 g; $C_4H_9Br$ 48.7 g; toluene 5.53 g; 50% NaOH solution 84.2 g; TEBA 1.14 g. The catalyst was used in suspension instead of in a fixed bed. K was found to be $5.45 \times 10^{-2}$.

EXAMPLE 4 (COMPARISON)

Example 2 was repeated using the following quantities: PAN 2.37 g; $C_4H_9Br$ 13.7 g; toluene 13.0 g; 50% NaOH solution 76.5 g; TEBA 2.57 g. The catalyst was used in suspension instead of in a fixed bed. K was found to be $1.63 \times 10^{-2}$.

Comparing K of Example 1 with K of Example 3 it will be noted that the values obtained when operating according to the invention are only slightly lower than those obtained operating with the catalyst in suspension. This latter however gives rise to the aforesaid drawbacks. The K values of Examples 2 and 4 when compared with that of Example 1 also show that the reactivity obtained without using ultrasound is much less than that obtainable when using ultrasound, whether the catalyst is in fixed bed or suspension.

EXAMPLE 5

Example 1 was repeated using the following quantities: PAN 33.9 g; $C_4H_9Br$ 197.3 g; toluene 8.63 g; 50% NaOH solution 273 g; TEBA 4.18 g. The operating temperature was 60° C. instead of 70° C. K was found to be $0.73 \times 10^{-2}$.

EXAMPLE 6

Example 1 was repeated using the following quantities: PAN 10.6 g; C$_4$H$_9$Br 62.8 g; toluene 9.93 g; 50% NaOH solution 107.1 g; TEBA 1.44 g, but with the difference that the apparatus of FIG. 5 was employed using treatment with a turbine rotating at 16,000 r.p.m. The operating temperature was 60° C. instead of 70° C. K was found to be $0.73 \times 10^{-2}$.

EXAMPLE 7

Example 1 was repeated using ultrasound treatment at a frequency of 20 KHz and a power of 150 W, with tributylbenzylammonium (hereinafter known as TBBA) bonded chemically to crosslinked polystyrene as catalyst. The conditions are as follows: PAN 30.0 g; C$_4$H$_9$Br 179 g; toluene 18.1 g; 50% NaOH solution 287 g; TBBA 4.26 g.

In this example, as in the subsequent, the reaction progress was monitored by determining the phenylacetonitrile conversion as a function of time. The conversion obtained in this example is shown by curve 1 of FIG. 6.

EXAMPLE 8

Example 7 was repeated using the following quantities: PAN 9.80 g; C$_4$H$_9$Br 56.7 g; toluene 5.40 g; 50% NaOH solution 91.9 g; TBBA 1.34 g, with ultrasound treatment at a frequency of 20 KHz and a power of 35 W. The conversion obtained is shown by curve 2 of FIG. 6.

EXAMPLE 9 (COMPARISON)

Example 8 was repeated using the following quantities: PAN 6.60 g; C$_4$H$_9$Br 33.2 g; toluene 3.19 g; 50% NaOH solution 53.4 g; TBBA 0.82 g. The device 2 with the catalyst 3 was not immersed in the liquid of the container 1 but was mounted externally to the container in the recirculation line.

Figure 6:
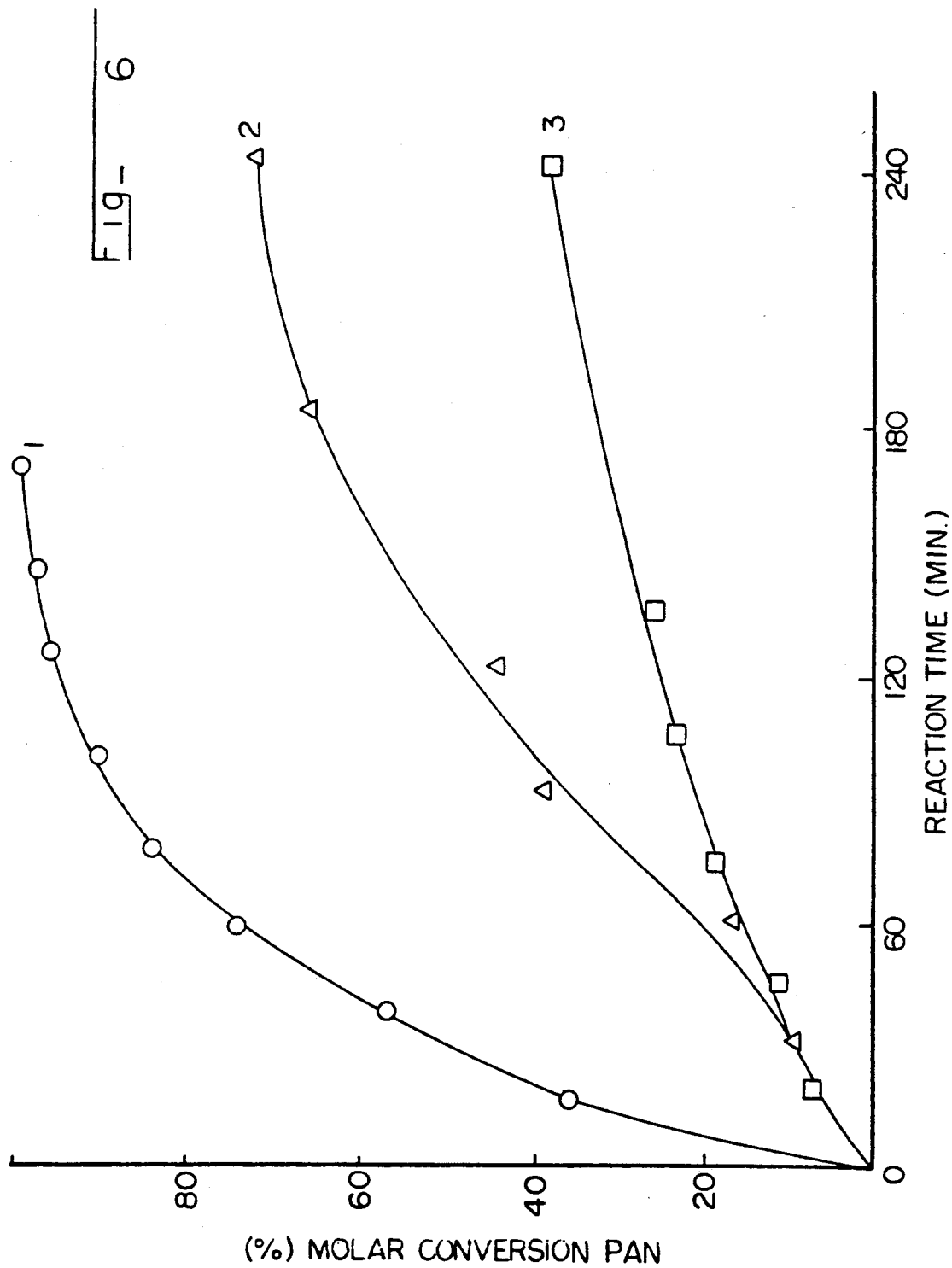
FIG. 6 shows the conversion of phenylacetonitrile with butyl bromide using ultrasound treatment with tributylbenzylammonium bound to cross-linked polystyrene as catalyst.

The conversion obtained, shown by curve 3 of FIG. 6, is much less than that of Example 8 conducted in accordance with the invention.

A comparison of Examples 8 and 9 shows the great advantage of reducing the distance between the emulsification zone and the reaction zone so as to obtain immediate contact between the emulsified liquid and the catalyst. A comparison of the results of Examples 7 and 8 also shows the need to deliver a sufficient power to the polyphase mixture, not only in terms of reactant mass/power ratio but also in terms of localized power concentration.

EXAMPLE 10

Example 1 was repeated using the following quantities: PAN 30.6 g; C$_4$H$_9$Br 179 g; toluene 17.5 g; 50% NaOH solution 286 g, but with the difference that the reaction was conducted without catalyst. The conversion obtained is represented by curve 1 of FIG. 7.

EXAMPLES 11 and 12 (COMPARISON)

Example 10 was repeated but with the difference that instead of using ultrasound treatment, the treatment was provided by agitation, using a magnetic bar rotating at 1000 r.p.m. and a turbine rotating at 7000 r.p.m., respectively.

Figure 7:
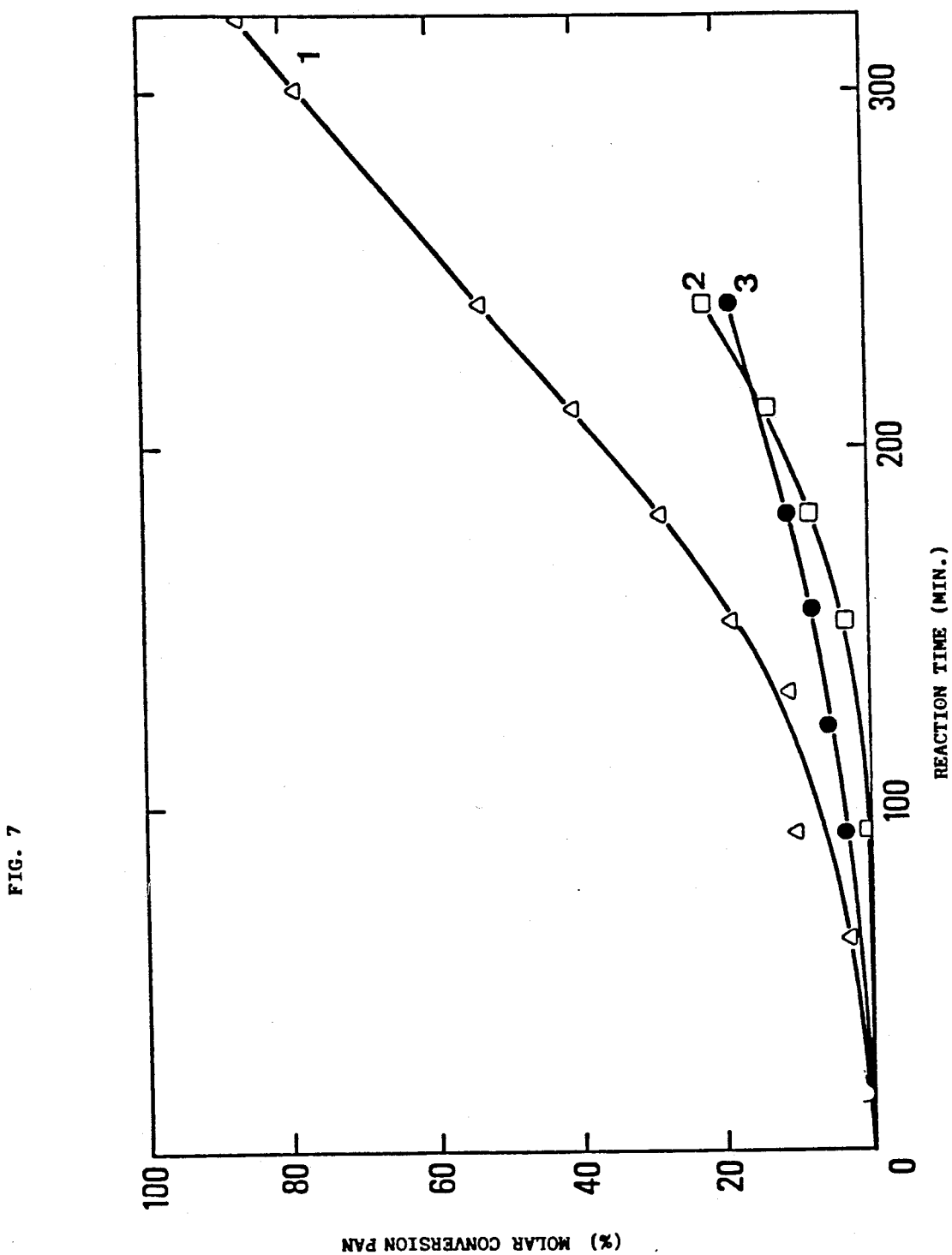
FIG. 7 shows the conversion of phenylacetonitrile with butyl bromide using ultrasound treatment without a catalyst.

The conversions are represented by curves 2 and 3 of FIG. 7, respectively.

For the test represented by curve 2 the conditions were as follows: PAN 31.5 g; C$_4$H$_9$Br 180.6 g; toluene 18.3 g; 50% NaOH solution 273.8 g. For the test represented by curve 3 the conditions were as follows: PAN 28.6 g; C$_4$H$_9$Br 180.9 g; toluene 17.9 g; 50% NaOH solution 278.5 g.

From these comparative examples it can be seen that when no catalyst is used, high conversions can be obtained only by using ultrasound treatment.

Examples 13, 14 and 15 relate to ethylation of PAN instead of its butylation described heretofore.

EXAMPLE 13

12.03 g of phenylacetonitrile, 60.94 g of ethylbromide (indicated hereinafter as C$_2$H$_5$Br) and 5.40 g of toluene as solvent were fed into the container 1 of the apparatus of FIGS. 1 and 3, and 91.80 g of a 50% w/w NaOH solution were added to this mixture.

The catalyst 3 in fixed bed form consisted of 1.60 g of TBBA bonded chemically to crosslinked polystyrene.

The liquid mixture was heated to 50° C., subjected to ultrasound treatment at a frequency of 20 KHz and a power of 35 W, and circulated through the catalyst 3 at a flow rate of 10 liters/hour.

Figure 8:
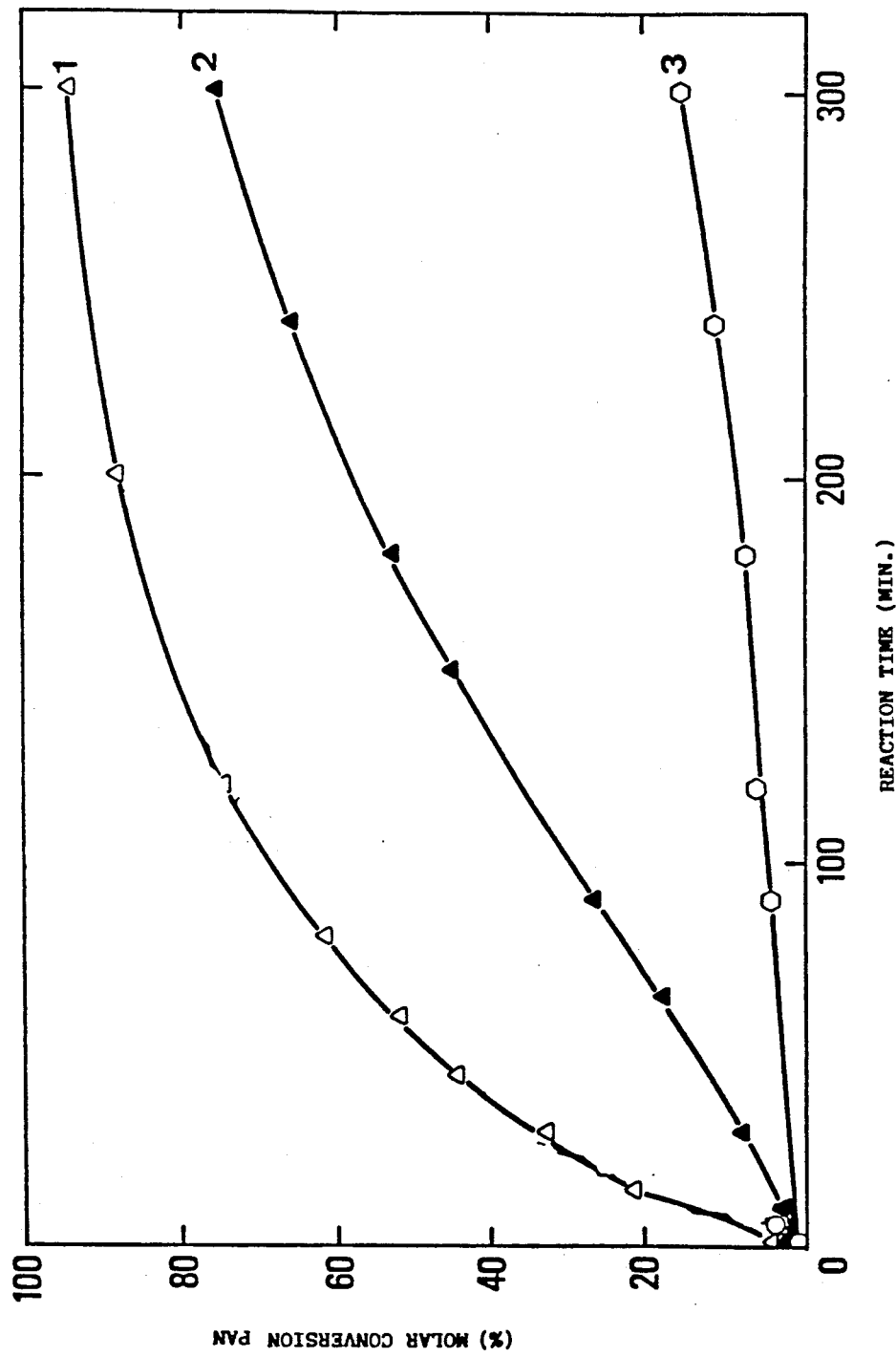
FIG. 8 shows the conversion of phenylacetonitrile with ethyl bromide using ultrasound treatment with tributylbenzylammonium bound to cross-linked polystyrene as catalyst.

The phenylacetonitrile conversion as a function of time is represented by curve 1 of FIG. 8.

EXAMPLE 14

Example 13 was repeated using the following quantities: PAN 10.90 g; C$_2$H$_5$Br 51.50 g; toluene 4.30 g; 50% NaOH solution 76.5 g. The reaction was conducted in the absence of catalyst and the ultrasound treatment was combined with agitation by means of a magnetic bar rotating at 1000 r.p.m.

As catalyst was not used, there was no external recirculation of the liquid reactants. The reactor was therefore that of FIG. 1 but without the catalyst holder 2. The conversion is represented by curve 2 of FIG. 8.

EXAMPLE 15 (COMPARISON)

Example 14 was repeated using the following quantities: PAN 11.0 g; C$_2$H$_5$Br 52.1 g; toluene 4.50 g; 50% NaOH solution 80.3 g. There was no ultrasound treatment, but only agitation by the magnetic bar rotating at 1000 r.p.m. The conversion is represented by curve 3 of FIG. 8.

A comparison of this curve with curve 2 of Example 14 shows that when operating without catalyst, interesting conversion levels can be obtained only by using ultrasound treatment.

I claim:

1. A method of conducting chemical reactions in polyphase systems, comprising the steps of:
    emulsifying liquid components, which consist of at least two partially or totally immiscible liquids, with an ultrasound emitter or a turbine;
    continuously circulating said emulsified liquid components; and
    directly contacting said emulsified liquid components with a solid catalyst arranged in a fixed bed; wherein said circulation is implemented at a throughput of between 0.1 and 100 l/h per g of said catalyst.

2. The method of claim 1, wherein the step of emulsification with said ultrasound emitter is conducted at a frequency of between 5-500 KHz.

3. The method of claim 1, wherein the step of emulsification with a turbine is conducted at a rotational speed of between 2000-25,000 r.p.m.

4. The method of claim 1, wherein the step of emulsification with said ultrasound emitter is implemented when said ultrasound emitter is disposed in said liquid components.

5. The method of claim 1, wherein the step of emulsification with said ultrasound emitter is implemented when said ultrasound emitter acts through a wall which is in contact with said liquid components.

* * * * *